US012347925B1

(12) United States Patent
Baldwin et al.

(10) Patent No.: US 12,347,925 B1
(45) Date of Patent: Jul. 1, 2025

(54) RADIO FREQUENCY ANTENNA FOR WEARABLE DEVICE

(71) Applicant: AMAZON TECHNOLOGIES, INC., Seattle, WA (US)

(72) Inventors: Leo Benedict Baldwin, Seattle, WA (US); David Heckerman, Bellevue, WA (US)

(73) Assignee: AMAZON TECHNOLOGIES, INC., Seattle, WA (US)

( * ) Notice: Subject to any disclaimer, the term of this patent is extended or adjusted under 35 U.S.C. 154(b) by 0 days.

(21) Appl. No.: 16/451,978

(22) Filed: Jun. 25, 2019

(51) Int. Cl.
| | | |
|---|---|---|
| H01Q 1/27 | (2006.01) | |
| A61B 5/05 | (2021.01) | |
| H01Q 7/00 | (2006.01) | |
| H01Q 21/06 | (2006.01) | |
| H01Q 21/28 | (2006.01) | |
| H01Q 25/04 | (2006.01) | |
| H04B 13/00 | (2006.01) | |

(52) U.S. Cl.
CPC .............. *H01Q 1/273* (2013.01); *H01Q 7/00* (2013.01); *H01Q 21/065* (2013.01); *H01Q 21/28* (2013.01); *H01Q 25/04* (2013.01); *H04B 13/005* (2013.01)

(58) Field of Classification Search
CPC ........ H01Q 7/00; H01Q 1/273; H04B 13/005; A61B 5/05
See application file for complete search history.

(56) References Cited

U.S. PATENT DOCUMENTS

| | | | | |
|---|---|---|---|---|
| 9,867,139 | B1 * | 1/2018 | Khasgiwala | H04B 17/318 |
| 10,868,356 | B1 * | 12/2020 | Da Costa Bras Lima | H01Q 5/321 |
| 11,058,331 | B1 * | 7/2021 | Bosua | H01Q 1/525 |
| 11,193,923 | B2 * | 12/2021 | Bosua | G01N 33/48707 |
| 11,284,820 | B1 * | 3/2022 | Bosua | G16H 50/70 |
| 11,857,304 | B1 * | 1/2024 | Baldwin | A61B 5/0507 |
| 12,029,557 | B1 * | 7/2024 | Kenny | H04B 17/104 |
| 12,092,589 | B1 * | 9/2024 | Bosua | H01Q 21/06 |
| 12,146,841 | B2 * | 11/2024 | Bosua | G01N 22/00 |
| 12,156,716 | B1 * | 12/2024 | Napoles | A61B 5/681 |
| 2003/0036674 | A1 * | 2/2003 | Bouton | H01Q 9/0414 600/12 |
| 2003/0036713 | A1 * | 2/2003 | Bouton | A61B 5/411 600/587 |

(Continued)

*Primary Examiner* — Ab Salam Alkassim, Jr.
(74) *Attorney, Agent, or Firm* — Lindauer Law, PLLC

(57) ABSTRACT

Data about concentration of one or more types of molecules present within a human body are determined noninvasively using radio frequency signals. These signals at several different frequencies are generated at very low power levels are emitted and acquired using an antenna mounted to a wearable device. Information about changes to the signals, such as phase variances of the signals at different frequencies is indicative of the concentration of one or more types molecules within the user. The antenna includes concentric elements with one or more being used to emit the signal(s) while one or more are used to acquire the signal(s). Concentrations at different depths may be measured by selectively using particular concentric elements. A maximum depth may approximately equal the spacing between the elements being used at a given time. Other sensors may be emplaced or operate through windows located between one or more of the concentric elements.

20 Claims, 7 Drawing Sheets

(56) References Cited

U.S. PATENT DOCUMENTS

| | | | | |
|---|---|---|---|---|
| 2008/0042903 | A1* | 2/2008 | Cheng | H01Q 9/0485 |
| | | | | 343/700 MS |
| 2014/0269977 | A1* | 9/2014 | Yang | H04B 7/0413 |
| | | | | 375/295 |
| 2015/0318624 | A1* | 11/2015 | Schantz | H01Q 7/00 |
| | | | | 343/867 |
| 2019/0053741 | A1* | 2/2019 | Chaudhry | A61B 5/6831 |
| 2019/0069399 | A1* | 2/2019 | Yoshida | H01Q 7/00 |
| 2019/0317177 | A1* | 10/2019 | Ertan | G01S 3/46 |
| 2020/0138304 | A1* | 5/2020 | Ozawa | A61B 5/1495 |
| 2020/0193326 | A1* | 6/2020 | Leabman | H01Q 21/061 |
| 2020/0195293 | A1* | 6/2020 | Leabman | H04B 1/3888 |
| 2020/0212985 | A1* | 7/2020 | Lin | H04B 7/0671 |
| 2021/0075094 | A1* | 3/2021 | Da Costa Bras Lima | |
| | | | | H04B 5/26 |
| 2021/0275049 | A1* | 9/2021 | Tao | H01Q 9/0485 |
| 2021/0275050 | A1* | 9/2021 | Ren | A61B 5/363 |
| 2021/0328338 | A1* | 10/2021 | Da Costa Bras Lima | |
| | | | | H01Q 5/385 |
| 2022/0192509 | A1* | 6/2022 | Leabman | A61B 5/14532 |
| 2022/0192510 | A1* | 6/2022 | Leabman | H01Q 1/273 |
| 2022/0192511 | A1* | 6/2022 | Leabman | H01Q 1/273 |
| 2022/0192522 | A1* | 6/2022 | Leabman | A61B 5/14532 |
| 2023/0299476 | A1* | 9/2023 | Lee | H01Q 3/245 |
| | | | | 606/33 |

* cited by examiner

RADIO FREQUENCY ANTENNA FOR WEARABLE DEVICE

BACKGROUND

Physiological data may be used to help a user manage their health, make more informed decisions, and improve the quality of their life. For example, physiological data such as hydration level, glucose concentration, and so forth may be useful for health management.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

Figure 1:
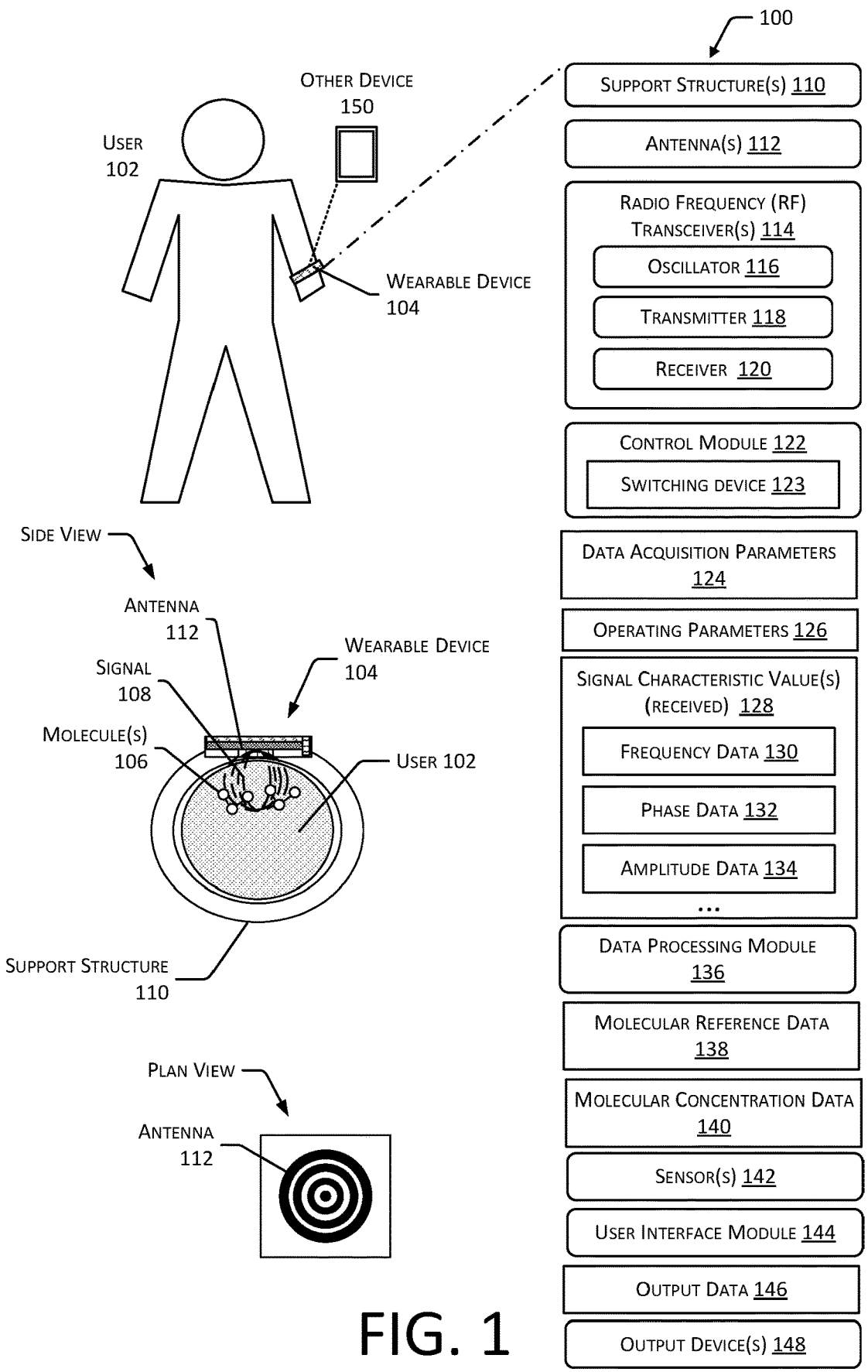
FIG. 1 is an illustrative system that includes a wearable device with an antenna that uses radio frequency signals to determine molecular concentrations of molecules of interest in the user, according to one implementation.

While implementations are described herein by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including, but not limited to.

DETAILED DESCRIPTION

The human body utilizes many different kinds of molecules to function. For example, glucose provides energy for cellular activity while water provides a medium to carry molecules such as glucose and also acts as a reactant. Other molecules may be introduced into the body. For example, alcohol may be consumed, carbon monoxide may be inhaled, a pesticide may be absorbed through the skin, and so forth.

Information about the concentration of one or more types of molecules within the tissues of the body is useful in many situations. For example, a person who is diabetic needs to know the concentration of glucose in their blood in order to keep that concentration in a healthy range. In another example, an athlete needs to make sure they are sufficiently hydrated to maximize their physical performance and avoid injury due to dehydration. Continuing the example, the athlete may also want to monitor their sodium and potassium levels to maintain an optimal level of electrolytes.

Traditionally information about the concentration of one or more types of molecules has been obtained through invasive measurement of a sample obtained from the person. For example, to measure glucose levels a sample of blood is taken and applied to a chemical test strip. In another example, a rough estimate of dehydration can be obtained by assessing skin turgor, such as by pinching the skin on the back of the hand. However, traditional methods have significant drawbacks. Obtaining samples of blood or other tissues within the body requires piercing the skin, injuring the person and introducing a possibility of infection. Additionally, such testing can be costly due to special handling consideration, use of consumables such as reagents, and so forth. Mechanical measurements, such as assessment of skin turgor, lack precision.

Described in this disclosure is an antenna that facilitates non-invasively measuring molecular concentration of one or more types of molecules within a user. The antenna comprises several different elements, which may be arranged around one another. For example, the antenna may comprise a central antenna element surrounded by other antenna elements in concentric rings.

By selectively using particular antenna elements, information may be obtained from different sample depths within the user. The distance between an antenna element used to emit a radio frequency signal (signal) and an antenna element used to acquire the signal affects how far within the user the signal penetrates while still providing a useful signal. For example, the central antenna element may be used to emit a first signal while an outermost antenna element comprising a ring which is 10 millimeters (mm) in diameter is used to acquire the first signal. Given the diameter of 10 mm, the first signal may be expected to penetrate and provide information on the tissue in the user from the surface to a first sample depth of approximately 10 mm. By sending and receiving signals using different antenna elements, data may be acquired from different sample depths. Continuing the example, the antenna may include a middle antenna element comprising a ring that is 5 mm in diameter that is located between the central antenna element and the outermost antenna element. The central antenna element may be used to emit a second signal while the middle antenna element acquires the second signal. As a result of the smaller diameter, the second signal provides information about a second sample depth of approximately 5 mm.

In other implementations the antenna may be used to provide information about a relatively large area but a relatively shallow depth. For example, the outermost antenna element may be used to emit the signal while the middle antenna element is used to acquire the signal. In this configuration the signal may provide information about the uppermost layers of the skin.

The antenna is able to operate in conjunction with other sensors. Apertures for, or other sensor elements, may be arranged between the antenna elements. For example, the antenna elements may be on a substrate. One or more apertures in the substrate between the central antenna element and the innermost antenna element may provide a window for other sensors to operate. For example, for an optical heart rate monitor may operate by sensing the user's skin using light sent through the aperture. In another example other sensors such as an optical emitter and an optical receiver may be located on the substrate between the antenna elements. In some implementations sensors may operate through the substrate.

During operation of the system, a radio frequency transmitter generates a first signal that is emitted from one or more antenna elements of the antenna. One or more other antenna elements of the antenna are used to acquire the first signal, which is detected using a radio frequency receiver. One or more signal characteristic values are determined. For example, the signal characteristic values may be indicative of a frequency of the received signal, a phase difference between the signal as transmitted and the signal as received, amplitude of the received signal, and so forth. Signals may be transmitted and received in different frequency bands, providing signal characteristic values for the different bands. For example, a first signal may be transmitted at 5 GHz, a second signal at 10 GHz, a third signal at 50 GHz, a fourth signal at 100 GHz, and so forth.

The signal characteristic values may be compared to molecular reference data to determine one or more of presence of or concentration of one or more types of molecules present within the user. In one implementation, the phase differences at different frequencies may be used to determine a concentration of a type of molecule, such as glucose. For example, the molecular concentration data may describe a linear relationship between phase differences at particular frequencies and glucose concentration. In other implementations, the concentration of other types of molecules may be determined. For example, the concentration of water may be determined, providing information about a hydration level of the user.

Overall exposure to radio frequency (RF) signals is limited, as the output power is extremely low and duration of the radio frequency (RF) signals may be very short. For example, the modulation of the signals may be continuous wave with a total duration of less than 1 millisecond (ms) and with a transmitter output power of 0 decibel-milliwatts (dBm). The sampling frequency, that is how often the RF signals are transmitted to gather data, may also be low, further reducing RF exposure. For example, the system may transmit signals once every six minutes, producing sets of ten samples per hour with each set comprising signal characteristic data for the various frequency bands.

By using the system with the antenna and techniques described in this disclosure, information about the concentration of various types of molecules at different depths within the user may be determined non-invasively. The ability to dynamically adjust the sample depth improves the ability for the system to obtain data. For example, due to anatomical differences, information about glucose levels may be obtained from a first user at a first sample depth and from a second user at a second sample depth. The system may use the antenna to acquire data from the sample depth that provides useful data. In another example, different molecules may be preferentially located at different depths. For example, hydration may be determined based on the presence of water in the upper layers of the skin at a relatively shallow sample depth while sodium concentration in the blood may be determined based on a relatively deep sample depth that includes larger arteries and veins.

The information provided by the system may be used to help diagnose, treat, or inform the user as to their physiological status. By acting on this information, the overall health of the user may be improved.

Illustrative System

FIG. 1 is an illustrative system 100 that may include a user 102 and a wearable device 104 that uses radio frequency (RF) signals to determine molecular concentrations of molecules of interest in at least a portion of the user's body, according to one implementation.

The user 102 may have one or more devices on or about their person, such as the wearable device 104. The wearable device 104 may be implemented in various physical form factors including, but not limited to, the following: wrist bands, torcs, arm bands, and so forth.

The user's 102 body contains one or more different types of molecules 106. For example, the blood of the user 102 may include glucose, water, creatinine, and so forth. Sometimes the body may include molecules 106 that are exogenous. For example, if the user 102 consumes alcohol, inhales carbon monoxide, absorbs a pesticide through the skin, and so forth, presence or concentration of those types of molecules 106 may be present in the dermis, within the blood, or other tissues within the body. As described below, a radio frequency (RF) signal 108 may be used to determine information about one or more molecules 106.

The wearable device 104 may include at least one support structure 110 that supports one or more of the following components. For example, the wearable device 104 may comprise a housing or capsule that is attached to a wrist band, allowing the wearable device 104 to be retained on the wrist of the user 102.

The wearable device 104 includes one or more antennas 112. The antennas 112 may comprise one or more antenna elements in particular arrangements. For example, the antenna elements may comprise a first antenna element and one or more antenna elements that are arranged around the first antenna element. The arrangement of antenna elements is discussed in more detail below with regard to FIGS. 4 and 5.

The antenna elements within a particular antenna 112 are connected to one or more radio frequency (RF) transceivers 114. In one implementation each antenna 112 may be connected to a particular transceiver 114. In other implementations, a single transceiver 114 may be connected via a switching device 123 comprising a switching network to two or more antennas 112.

The transceiver 114 may comprise an oscillator 116, a transmitter 118, and a receiver 120. The oscillator 116 may be used to provide a reference frequency for operation of the transmitter 118, the receiver 120, a clock (not shown), and so forth. The transmitter 118 is configured to generate the RF signal 108. The transmitter 118 may be able to generate RF signals 108 at one or more frequencies, in one or more frequency bands or ranges, and so forth. For example, the transmitter 118 may be able to generate RF signals 108 at one or more of the 5 GHz, 10 GHz, 50 GHz, 75 GHz, 100 GHz, or other bands. The RF signal 108 that is generated may be modulated with a continuous wave.

During transmission, the transmitter 118 provides the RF signal 108 to one or more of the antenna elements in one or more antennas 112. For example, output from the transmitter 118 may be connected to a first antenna element in the antenna 112. The antennas 112 emit the signal 108 which then impinges on the body of the user 102 while the device 104 is being worn or held close to the user 102.

In some implementations, during reception, one or more of the antenna elements in the antenna 112 that are not connected to the transmitter 118 are connected to an input of the receiver 120. Continuing the example above, the receiver 120 may be connected to the second antenna element in the antenna 112. The receiver 120 detects the RF signal 108. The receiver 120 may comprise analog hardware, digital hardware, or a combination thereof. For example, the receiver 120 may comprise a direct sampling software defined radio (SDR). In another example, the RF signal 108 as acquired by the one or more antenna elements of the one or more antennas 112 may be mixed with output from the oscillator 116. In other implementations the same antenna element of the antenna 112 may be connected to the transmitter 118 and the receiver 120 simultaneously using one or more directional couplers, duplexers, or other devices.

The transceiver 114 may be configurable to operate in simplex, duplex, or combinations thereof. For example, the transceiver 114 may be configurable to transmit on one band while receiving on another band. In one implementation, the transceiver 114 may comprise the BGT24LTR11 device from Infineon Technologies AG that is capable of transmitting and receiving in the 24 GHz band.

While transceivers 114 are shown, it is understood that in other implementations other components such as a discrete transmitter 118 and receiver 120 could be used.

A control module 122 may be used to direct operation of the transceivers 114 or other components. For example, the control module 122 may comprise a hardware processor (processor) executing instructions that operate one or more of the transmitters 118 to transmit particular signals at particular frequencies at particular times, to operate one or more of the receivers 120 to receive the signals generated by the one or more transmitters 118, to operate switching device 123 or other circuitry to connect particular antenna elements to the transmitter 118 output, to operate switching device 123 or other circuitry to connect particular antenna elements to the input of the receiver 120, and so forth.

The control module 122 may use one or more data acquisition parameters 124 to control operation. For example, the data acquisition parameters 124 may specify a sample frequency that indicates how often to transmit and receive signals, sample depth within the user 102 to be used, and so forth. In some implementations the data acquisition parameters 124 may be specific to a particular type of molecule 106 that is being detected. For example, the data acquisition parameters 124 for glucose may have a first sample depth that is different from a second sample depth used for organophosphates. The data acquisition parameters 124 may reference specific operating parameters 126.

The operating parameters 126 may specify one or more of frequency, output power, modulation, signal duration, particular antenna elements used to emit the signal 108, particular antenna elements used to acquire the signal 108, and so forth. For example, the operating parameters 126 may specify that a signal is to be transmitted with a center frequency of 5.201 GHz at 0 dBm, continuous wave (CW) modulation, for 1 ms using a chirp with ascending frequency from 5.200 to 5.202 GHz, emitted from a central antenna element and acquired using a third antenna element.

The operating parameters 126 may relate a sample depth specified by the data acquisition parameters 124 to a particular antenna configuration. For example, the data acquisition parameters 124 may indicate a depth in terms of linear measurement such as millimeters or with a relative indicator such as "shallow", "medium", or "deep". Responsive to the data acquisition parameters 124, the control module 122 may determine operating parameters that are indicative of a particular antenna configuration. For example, a "shallow" sample depth may correspond to an antenna configuration in which the first antenna element is used to emit the signal 108 while the second antenna element is used to acquire the signal 108. In comparison, a "deep" sample depth may correspond to an antenna configuration in which the first antenna element is used to emit the signal 108 while a fourth antenna element is used to acquire the signal 108.

Once the operating parameters 126 have been determined, the control module 122 or another component may operate the circuitry in the wearable device 104. For example, first circuitry may be operated to selectively couple the output from the transmitter 118 to the first antenna element and second circuitry may be operated to selectively couple the input to the receiver 120 to the second antenna element.

The receivers 120 produce signal characteristic values 128 that are representative of the received signals. The signal characteristic values 128 may include, but are not limited to, frequency data 130, phase data 132, amplitude data 134, and so forth. Frequency data 130 is indicative of frequency of the received signal. The phase data 132 provides information about the phase of the received signal, and in some implementations may be used to determine a phase difference between the transmitted signal and the received signal. The amplitude data 134 provides information indicative of amplitude of the received signal. For example, the amplitude data 134 may indicate a received signal strength at different frequencies. Other signal characteristic values 128 may include received signal polarization.

As the RF signals 108 pass through the body of the user 102, they are affected by the molecules 106 therein. Various interactions take place between the signals 108 and the molecules 106. For example, the presence of glucose in the body along the line extending from the antenna 112(1) that is emitting the signal 108 and the antenna 112(2) that is acquiring the signal 108 may result in a change in the phase of the received signal, relative to the transmitted signal. In some implementations, a phase difference that is indicative of this change in phase of the received signal relative to the transmitted signal, may be indicative of the concentration of glucose. For example, with no glucose present a 0 degree phase difference may be detected, while a 0.004 degree phase difference may be associated with the presence of glucose. As described below, a presence or concentration of a type of molecule 106 may be determined based on the phase difference or other signal characteristics.

A data processing module 136 may use one or more of the operating parameters 126 of the transmitted signal(s) or the signal characteristic values 128 of the received signal(s) as input. The data processing module 136 may also access molecular reference data 138. The molecular reference data 138 comprises information that, for a particular type of molecule 106, associates one or more signal characteristics with information such as concentration of the particular type of molecule 106. The molecular reference data 138 may be general or specific to a particular user 102. For example, the molecular reference data 138 may be generated and associated with particular user 102(1) "Pat".

The data processing module 136 uses the signal characteristic value(s) 128 and the molecular reference data 138 to determine molecular concentration data 140. The molecular concentration data 140 may specify a mass per unit volume. For example, the signal characteristic value 128 indicates the phase difference at a particular frequency is 0.004 degrees. This value may be used as input to the molecular reference data 138 which corresponds to molecular concentration data 140 indicative of a mass per volume, such as a glucose concentration of 159 milligrams per deciliter (md/dL).

As described below in more detail, the signal characteristic values 128 may be obtained for a plurality of different frequencies and may be obtained using a variety of different combinations of antennas 112 to emit and acquire the signals 108. The signal characteristic values 128 may be used to determine the molecular concentration data 140 for one or more different types of molecules 106. For example, the molecular concentration data 140 may indicate the concentration of glucose and water in the body of the user 102.

The wearable device 104 may include, or receive data from, one or more other sensors 142. For example, a temperature sensor may be used to provide an indication of the body temperature of the user 102. The body temperature may then be used as an input to the data processing module 136 to improve the accuracy of the molecular concentration data 140. These sensors 142 are discussed in more detail below with regard to FIG. 2. In other implementations data from the sensors 142 may be obtained to provide other information about physiological status, activity level, and so forth.

Output from the sensors 142 may also be used to determine operation of the data processing module 136. For example, the sensors 142 may include one or more accelerometers. If the accelerometers detect motion that exceeds a threshold value, the data processing module 136 may be operated to determine molecular concentration data 140. For example, if the user 102 has been running, the system may operate to determine glucose concentration. In another example, if the motion of the user 102 is less than a threshold value, the data processing module 136 may be operated to determine molecular concentration data 140. For example, if no movement has been detected for 2 minutes, such as if the user is asleep or unconscious, the data processing module 136 may be operated to determine molecular concentration data 140.

A user interface module 144 may be configured to use the molecular concentration data 140 and produce output data 146. For example, based on the molecular concentration data 140 indicating that the blood glucose level is below a threshold value, output data 146 may be generated. One or more output devices 148 may be used to present a user interface based on at least a portion of the output data 146. Continuing the example, the user interface module 144 may produce output data 146 that comprises instructions to operate a speaker to present an audible prompt indicating the low blood glucose level. In another example, the output data 146 may be provided to an other device 150. For example, the wearable device 104 may be connected via Bluetooth or another wireless protocol to a smartphone, wireless access point, in vehicle computer system, or other device. Based on the output data 146 the other device 150 may present an output to the user 102, alert someone else, modify operation of another device, and so forth. For example, if the wearable device 104 provides data to a vehicle that indicates the user 102 in the driver's seat has a concentration of alcohol that exceeds a threshold value, the vehicle may be prevented from moving, or may only be able to operate in a fully autonomous mode.

Figure 2:
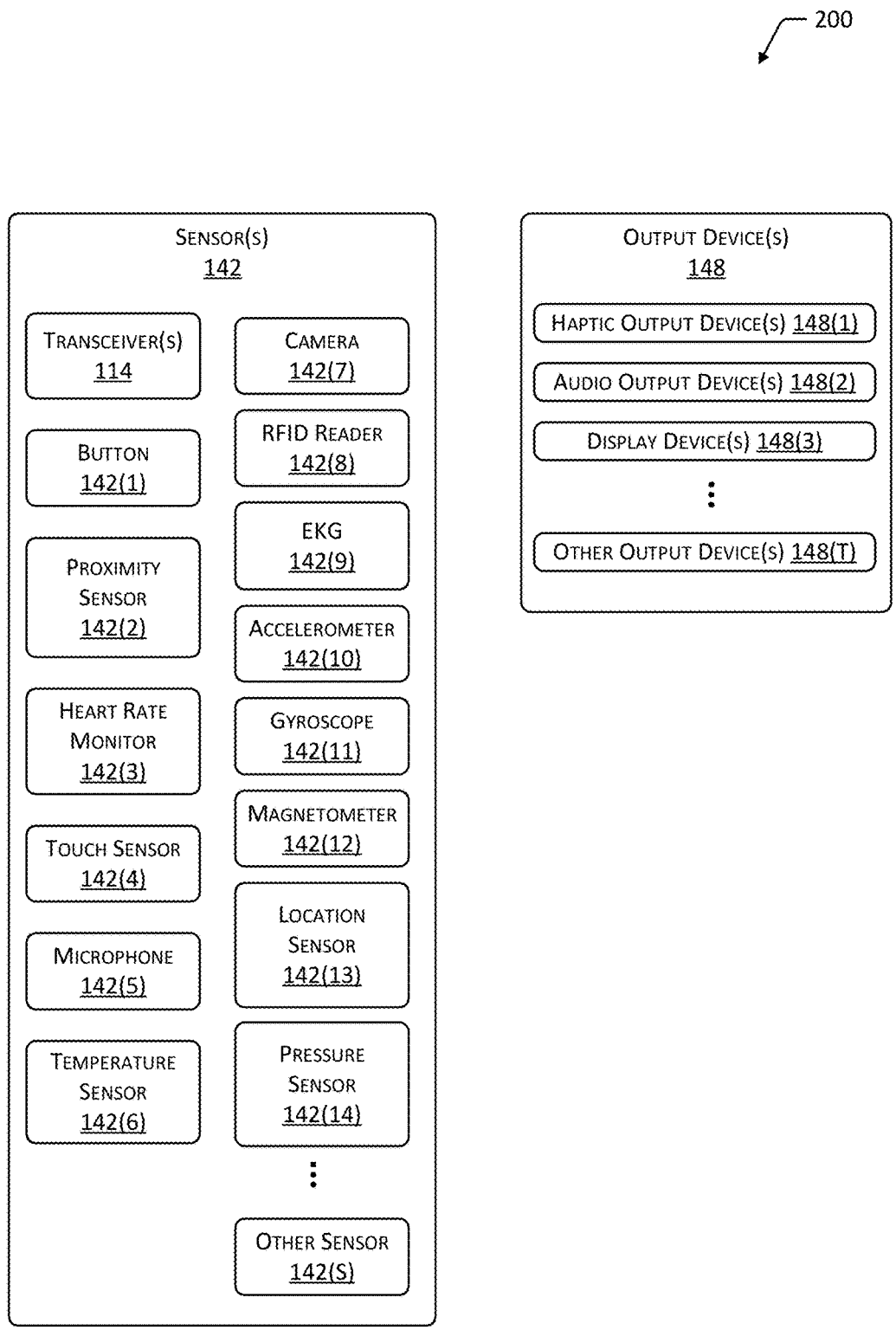
FIG. 2 illustrates a block diagram of sensors and output devices that may be used by computing device(s) during operation, according to one implementation.

FIG. 2 illustrates a block diagram 200 of sensors 142 and output devices 148 that may be used by the devices of the system 100 during operation.

The one or more sensors 142 may be integrated with or internal to the wearable device 104 or the other device 150. For example, the sensors 142 may be built-in to the wearable device 104 during manufacture. In other implementations, the sensors 142 may be part of another device which is in communication with the wearable device 104. For example, the sensors 142 may comprise a device external to, but in communication with, the wearable device 104 using Bluetooth, Wi-Fi, 3G, 4G, 5G, LTE, ZigBee, Z-Wave, or another wireless or wired communication technology.

The sensors 142 may include the transceivers 114.

The one or more sensors 142 may include one or more buttons 142(1) that are configured to accept input from the user 102. The buttons 142(1) may comprise mechanical, capacitive, optical, or other mechanisms. For example, the buttons 142(1) may comprise mechanical switches configured to accept an applied force from a touch of the user 102 to generate an input signal.

A proximity sensor 142(2) may be configured to provide sensor data 324 indicative of one or more of a presence or absence of an object, a distance to the object, or characteristics of the object. The proximity sensor 142(2) may use optical, electrical, ultrasonic, electromagnetic, or other techniques to determine a presence of an object. For example, the proximity sensor 142(2) may comprise a capacitive proximity sensor configured to provide an electrical field and determine a change in electrical capacitance due to presence or absence of an object within the electrical field.

A heart rate monitor 142(3) or pulse oximeter may be configured to provide sensor data 324 that is indicative of a cardiac pulse rate, and data indicative of oxygen saturation of the user's 102 blood, and so forth. For example, the heart rate monitor 142(3) may use an optical emitter such as one or more light emitting diodes (LEDs) and a corresponding optical detector such as a photodetector to perform photoplethysmography, determine cardiac pulse, determine changes in apparent color of the blood of the user 102 resulting from oxygen binding with hemoglobin in the blood, and so forth.

The sensors 142 may include one or more touch sensors 142(4). The touch sensors 142(4) may use resistive, capacitive, surface capacitance, projected capacitance, mutual capacitance, optical, Interpolating Force-Sensitive Resistance (IFSR), or other mechanisms to determine the position of a touch or near-touch of the user 102. For example, the IFSR may comprise a material configured to change electrical resistance responsive to an applied force. The location within the material of that change in electrical resistance may indicate the position of the touch.

One or more microphones 142(5) may be configured to acquire information about sound present in the environment. In some implementations, arrays of microphones 142(5) may be used. These arrays may implement beamforming techniques to provide for directionality of gain. The one or more microphones 142(5) may be used to acquire audio data, such as speech from the user 102.

A temperature sensor (or thermometer) 142(6) may provide information indicative of a temperature of an object. The temperature sensor 142(6) in may be configured to measure ambient air temperature proximate to the user 102, the body temperature of the user 102, and so forth. The temperature sensor 142(6) may comprise a silicon bandgap temperature sensor, thermistor, thermocouple, or other device. In some implementations, the temperature sensor 142(6) may comprise an infrared detector configured to determine temperature using thermal radiation.

The sensors 142 may include one or more cameras 142(7). The cameras 142(7) may comprise a charge couple device, complementary oxide semiconductor, or other image sensor that is able to acquire images.

One or more radio frequency identification (RFID) readers 142(8), near field communication (NFC) systems, and so forth, may also be included as sensors 142. The user 102, objects around the computing device, locations within a building, and so forth, may be equipped with one or more radio frequency (RF) tags. The RF tags are configured to emit an RF signal. In one implementation, the RF tag may be a RFID tag configured to emit the RF signal upon activation by an external signal. For example, the external signal may comprise a RF signal or a magnetic field configured to energize or activate the RFID tag. In another implementation, the RF tag may comprise a transmitter and a power source configured to power the transmitter. For example, the RF tag may comprise a Bluetooth Low Energy (BLE) transmitter and battery. In other implementations, the tag may use other techniques to indicate its presence. For example, an acoustic tag may be configured to generate an ultrasonic signal, which is detected by corresponding acoustic receivers. In yet another implementation, the tag may be configured to emit an optical signal.

The sensors 142 may include an electrocardiograph 142(9) that is configured to detect electrical signals produced by the heart of the user 102.

The sensors 142 may include one or more accelerometers 142(10). The accelerometers 142(10) may provide information such as the direction and magnitude of an imposed acceleration. Data such as rate of acceleration, determination of changes in direction, speed, and so forth, may be determined using the accelerometers 142(10).

A gyroscope 142(11) provides information indicative of rotation of an object affixed thereto. For example, the gyroscope 142(11) may indicate whether the device has been rotated.

A magnetometer 142(12) may be used to determine an orientation by measuring ambient magnetic fields, such as the terrestrial magnetic field. For example, output from the magnetometer 142(12) may be used to determine whether the device containing the sensor 142, such as a computing device, has changed orientation or otherwise moved. In other implementations, the magnetometer 142(12) may be configured to detect magnetic fields generated by another device.

A location sensor 142(13) is configured to provide information indicative of a location. The location may be relative or absolute. For example, a relative location may indicate "kitchen", "bedroom", "conference room", and so forth. In comparison, an absolute location is expressed relative to a reference point or datum, such as a street address, geolocation comprising coordinates indicative of latitude and longitude, grid square, and so forth. The location sensor 142(13) may include, but is not limited to, radio navigation-based systems such as terrestrial or satellite-based navigational systems. The satellite-based navigation system may include one or more of a Global Positioning System (GPS) receiver, a Global Navigation Satellite System (GLONASS) receiver, a Galileo receiver, a BeiDou Navigation Satellite System (BDS) receiver, an Indian Regional Navigational Satellite System, and so forth. In some implementations, the location sensor 142(13) may be omitted or operate in conjunction with an external resource such as a cellular network operator providing location information, or Bluetooth beacons.

A pressure sensor 142(14) may provide information about the pressure between a portion of the wearable device 104 and a portion of the user 102. For example, the pressure sensor 142(14) may comprise a capacitive element, strain gauge, spring-biased contact switch, or other device that is used to determine the amount of pressure between the user's 102 arm and an inner surface of the wearable device 104 that is in contact with the arm. In some implementations the pressure sensor 142(14) may provide information indicative of a force measurement, such as 0.5 Newtons, a relative force measurement, or whether the pressure is greater than a threshold value.

In some implementations, operation of one or more components in the wearable device 104 may be based at least in part on information from the pressure sensor 142(14). For example, based on data provided by the pressure sensor 142(14) a determination may be made as to whether at least a portion of the wearable device 104 is in contact with the user 102 or another object. Continuing the example, if the pressure indicated by the pressure sensor 142(14) exceeds a threshold value, the wearable device 104 may be determined to be in contact with the user 102. Based on this determination that the wearable device 104 is in contact with the user 102, one or more of the transmitter 118, receiver 120, sensors 142, and so forth may be operated. Likewise, data from the pressure sensor 142(14) may be used to determine the wearable device 104 is not in sufficient physical contact with the user 102. As a result, one or more of the transmitter 118, receiver 120, sensors 142, and so forth may be turned off.

The sensors 142 may include other sensors 142(S) as well. For example, the other sensors 142(S) may include strain gauges, anti-tamper indicators, and so forth. For example, strain gauges or strain sensors may be embedded within the wearable device 104 and may be configured to provide information indicating that at least a portion of the wearable device 104 has been stretched or displaced such that the wearable device 104 may have been donned or doffed.

In some implementations, the sensors 142 may include hardware processors, memory, and other elements configured to perform various functions. Furthermore, the sensors 142 may be configured to communicate by way of the network or may couple directly with the computing device.

The computing device may include or may couple to one or more output devices 148. The output devices 148 are configured to generate signals which may be perceived by the user 102, detectable by the sensors 142, or a combination thereof.

Haptic output devices 148(1) are configured to provide a signal, which results in a tactile sensation to the user 102. The haptic output devices 148(1) may use one or more mechanisms such as electrical stimulation or mechanical displacement to provide the signal. For example, the haptic output devices 148(1) may be configured to generate a modulated electrical signal, which produces an apparent tactile sensation in one or more fingers of the user 102. In another example, the haptic output devices 148(1) may comprise piezoelectric or rotary motor devices configured to provide a vibration that may be felt by the user 102.

One or more audio output devices 148(2) are configured to provide acoustic output. The acoustic output includes one or more of infrasonic sound, audible sound, or ultrasonic sound. The audio output devices 148(2) may use one or more mechanisms to generate the acoustic output. These mechanisms may include, but are not limited to, the following: voice coils, piezoelectric elements, magnetorestrictive elements, electrostatic elements, and so forth. For example, a piezoelectric buzzer or a speaker may be used to provide acoustic output by an audio output device 148(2).

The display devices 148(3) may be configured to provide output that may be seen by the user 102 or detected by a light-sensitive detector such as the image sensor or light sensor. The output may be monochrome or color. The display devices 148(3) may be emissive, reflective, or both. An emissive display device 148(3), such as using light emitting diodes (LEDs), is configured to emit light during operation. In comparison, a reflective display device 148(3), such as using an electrophoretic element, relies on ambient light to present an image. Backlights or front lights may be used to illuminate non-emissive display devices 148(3) to provide visibility of the output in conditions where the ambient light levels are low.

The display mechanisms of display devices 148(3) may include, but are not limited to, micro-electromechanical systems (MEMS), spatial light modulators, electroluminescent displays, quantum dot displays, liquid crystal on silicon (LCOS) displays, cholesteric displays, interferometric displays, liquid crystal displays, electrophoretic displays, LED displays, and so forth. These display mechanisms are configured to emit light, modulate incident light emitted from another source, or both. The display devices 148(3) may operate as panels, projectors, and so forth.

The display devices 148(3) may be configured to present images. For example, the display devices 148(3) may comprise a pixel-addressable display. The image may comprise at least a two-dimensional array of pixels or a vector representation of a two-dimensional image.

In some implementations, the display devices 148(3) may be configured to provide non-image data, such as text or numeric characters, colors, and so forth. For example, a segmented electrophoretic display device, segmented LED, and so forth, may be used to present information such as letters or numbers. The display devices 148(3) may also be configurable to vary the color of the segment, such as using multicolor LED segments.

Other output devices 148(T) may also be present. For example, the other output devices 148(T) may include scent/odor dispensers.

Figure 3:
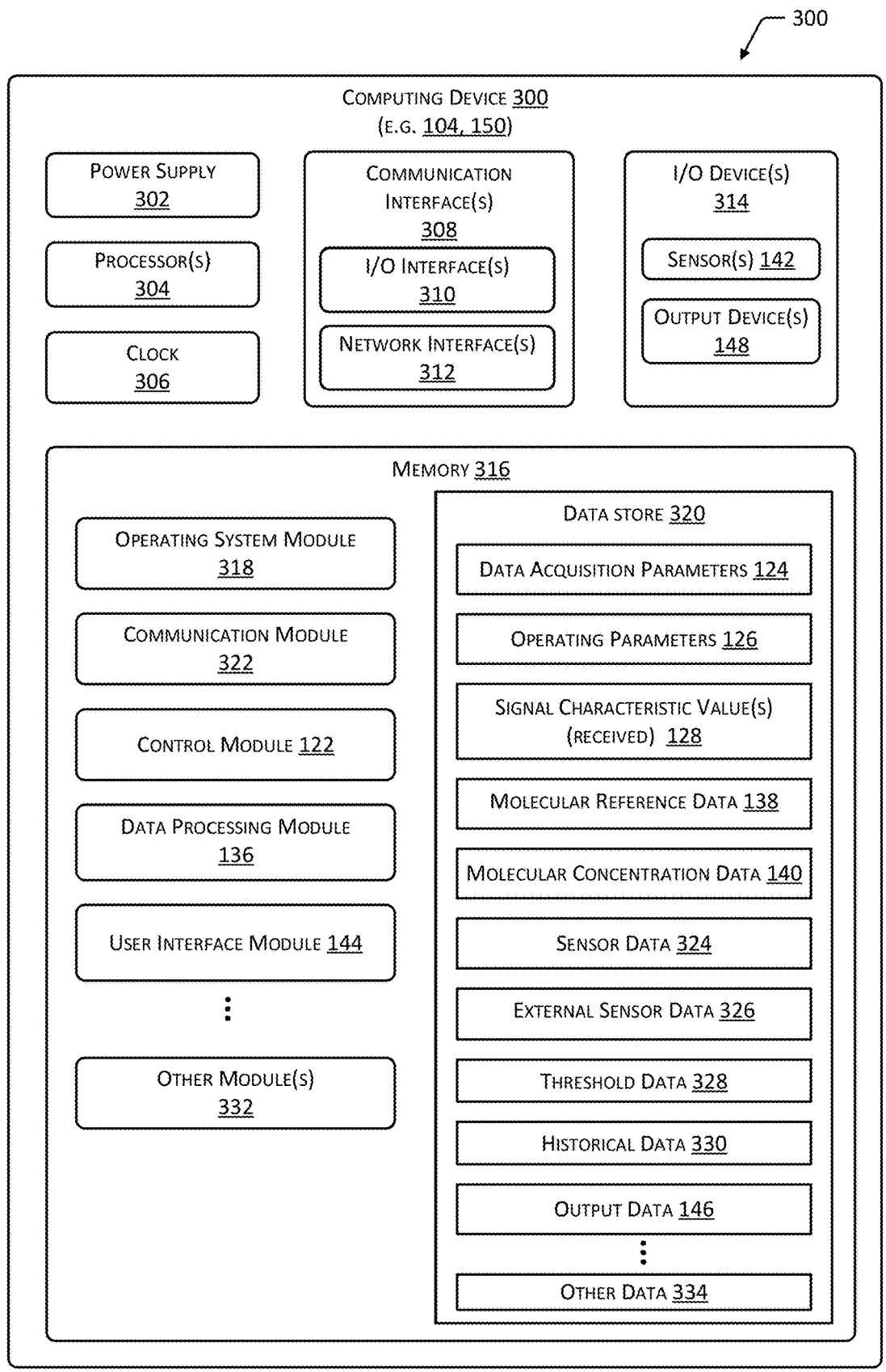
FIG. 3 illustrates a block diagram of a computing device(s) that may be included in or in communication with the measurement device, according to one implementation.

FIG. 3 illustrates a block diagram of a computing device 300 configured to support operation of the system 100. As described above, the computing device 300 may be the wearable device 104, the other device 150, and so forth.

One or more power supplies 302 are configured to provide electrical power suitable for operating the components in the computing device 300. In some implementations, the power supply 302 may comprise a rechargeable battery, fuel cell, photovoltaic cell, power conditioning circuitry, and so forth.

The computing device 300 may include one or more hardware processors 304 (processors) configured to execute one or more stored instructions. The processors 304 may comprise one or more cores. One or more clocks 306 may provide information indicative of date, time, ticks, and so forth. For example, the processor 304 may use data from the clock 306 to generate a timestamp, trigger a preprogrammed action, and so forth.

The computing device 300 may include one or more communication interfaces 308 such as input/output (I/O) interfaces 310, network interfaces 312, and so forth. The communication interfaces 308 enable the computing device 300, or components thereof, to communicate with other devices or components. The communication interfaces 308 may include one or more I/O interfaces 310. The I/O interfaces 310 may comprise interfaces such as Inter-Integrated Circuit (I2C), Serial Peripheral Interface bus (SPI), Universal Serial Bus (USB) as promulgated by the USB Implementers Forum, RS-232, and so forth.

The I/O interface(s) 310 may couple to one or more I/O devices 314. The I/O devices 314 may include input devices such as one or more of a camera 142(7), a sensor 142, keyboard, mouse, scanner, and so forth. The I/O devices 314 may also include output devices 148 such as one or more of a display device 148(3), printer, audio output device 148(2), and so forth. In some embodiments, the I/O devices 314 may be physically incorporated with the computing device 300 or may be externally placed.

The network interfaces 312 are configured to provide communications between the computing device 300 and other devices, such as the sensors 142, routers, access points, and so forth. The network interfaces 312 may include devices configured to couple to wired or wireless personal area networks (PANs), local area networks (LANs), wide area networks (WANs), and so forth. For example, the network interfaces 312 may include devices compatible with Ethernet, Wi-Fi, Bluetooth, ZigBee, 4G, 5G, LTE, and so forth.

The computing device 300 may also include one or more busses or other internal communications hardware or software that allow for the transfer of data between the various modules and components of the computing device 300.

As shown in FIG. 3, the computing device 300 includes one or more memories 316. The memory 316 comprises one or more computer-readable storage media (CRSM). The CRSM may be any one or more of an electronic storage medium, a magnetic storage medium, an optical storage medium, a quantum storage medium, a mechanical computer storage medium, and so forth. The memory 316 provides storage of computer-readable instructions, data structures, program modules, and other data for the operation of the computing device 300. A few example functional modules are shown stored in the memory 316, although the same functionality may alternatively be implemented in hardware, firmware, or as a system on a chip (SOC).

The memory 316 may include at least one operating system (OS) module 318. The OS module 318 is configured to manage hardware resource devices such as the I/O interfaces 310, the network interfaces 312, the I/O devices 314, and provide various services to applications or modules executing on the processors 304. The OS module 318 may implement a variant of the FreeBSD operating system as promulgated by the FreeBSD Project; other UNIX or UNIX-like operating system; a variation of the Linux operating system as promulgated by Linus Torvalds; the Windows operating system from Microsoft Corporation of Redmond, Wash., USA; the Android operating system from Google Corporation of Mountain View, Calif., USA; the iOS operating system from Apple Corporation of Cupertino, Calif., USA; or other operating systems.

Also stored in the memory 316 may be a data store 320 and one or more of the following modules. These modules may be executed as foreground applications, background tasks, daemons, and so forth. The data store 320 may use a flat file, database, linked list, tree, executable code, script, or other data structure to store information. In some implementations, the data store 320 or a portion of the data store 320 may be distributed across one or more other devices including the computing devices 300, network attached storage devices, and so forth.

A communication module 322 may be configured to establish communications with one or more of other computing devices 300, the sensors 142, or other devices 150. The communications may be authenticated, encrypted, and so forth. The communication module 322 may also control the communication interfaces 308.

One or more of the data acquisition parameters 124, operating parameters 126, signal characteristic values 128, molecular reference data 138, or the molecular concentration data 140 may be stored in the memory 316.

The memory 316 may also store the control module 122. As described above, the control module 122 may operate the transceivers 114 to produce signal characteristic values 128.

The memory 316 may store the data processing module 136. The data processing module 136 uses the signal characteristic values 128, the molecular reference data 138, and so forth as input to generate the molecular concentration data 140.

In one implementation, the data processing module 136 may use molecular reference data 138 to generate molecular concentration data 140 that is indicative of a concentration of one or more types of molecules 106 in the user 102.

In some implementations, a calibration process may be performed in which an external sensor is used to obtain external sensor data 326 that is indicative of a concentration of a type of molecule 106. For example, a blood glucose meter that uses a sample of a drop of blood may be used as the external sensor. At a contemporaneous time, the transceivers 114 may be used to obtain the signal characteristic values 128. The external sensor data 326 comprising concentration data from the external sensor may be used in conjunction with the signal characteristic values 128 to determine a correspondence between one or more signal characteristic values 128 and molecular concentration. This correspondence may be stored as the molecular reference data 138. The molecular reference data 138 may be specific to a particular user 102. For example, the molecular reference data 138 may be specific to user "Pat". In some implementations, the molecular reference data 138 may be processed using one or more techniques to interpolate values between those which have been measured. In some implementations, previously acquired molecular reference data 138 may be used, and a calibration factor may be determined based on the molecular reference data 138.

Threshold data 328 may be stored in the memory 316. The threshold data 328 may be used to designate a threshold to which molecular concentration data 140 may be compared. For example, the threshold data 328 may specify threshold values for particular types of molecules 106. If the molecular concentration data 140 is less than a first threshold or greater than a second threshold, the user interface module 144 may generate an alarm and present that information using the output device 148.

The user interface module 144 provides a user interface using one or more of the I/O devices 314. The user interface module 144 may be used to obtain input from the user 102, present information to the user 102, and so forth. For example, the user interface module 144 may present a graphical user interface on the display device 148(3) and accept user input using the touch sensor 142(4).

Continuing the earlier example, if the molecular concentration data 140 indicates that user's 102 blood glucose level is less than a threshold value, the user interface module 144 may present information indicative of this on the display device 148(3). The user 102 may then take corrective actions, such as consuming glucose to raise their blood sugar level, reducing activity, and so forth.

The computing device 300 may maintain historical data 330. For example, the historical data 330 may comprise the signal characteristic values 128, molecular concentration data 140, or data from one or more of the sensors 142 obtained at different times. The historical data 330 may be used to provide information about trends or changes over time. For example, the historical data 330 may comprise an indication of average daily blood glucose levels of the user 102 over a span of several weeks. The user 102 may then use this data to assist in managing their diet and insulin dosage.

Other modules 332 may also be present in the memory 316, as well as other data 334 in the data store 320.

In different implementations, different computing devices 300 may have different capabilities or capacities. For example, the other device 150 may have significantly more processor 304 capability and memory 316 capacity compared to the wearable device 104. In one implementation, the wearable device 104 may determine the signal characteristic values 128 and send those values to the other device 150. Other combinations of distribution of data processing and functionality may be used in other implementations.

Figure 4:
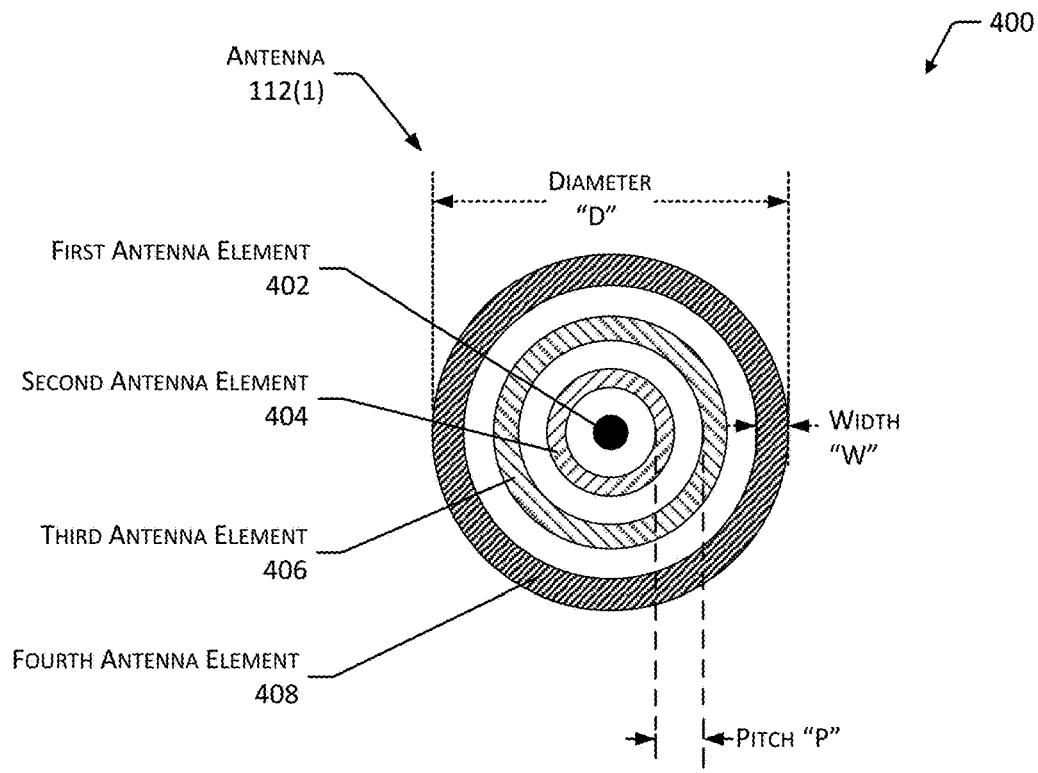
FIG. 4 illustrates some implementations of antenna elements in the antenna.
Figure 4:
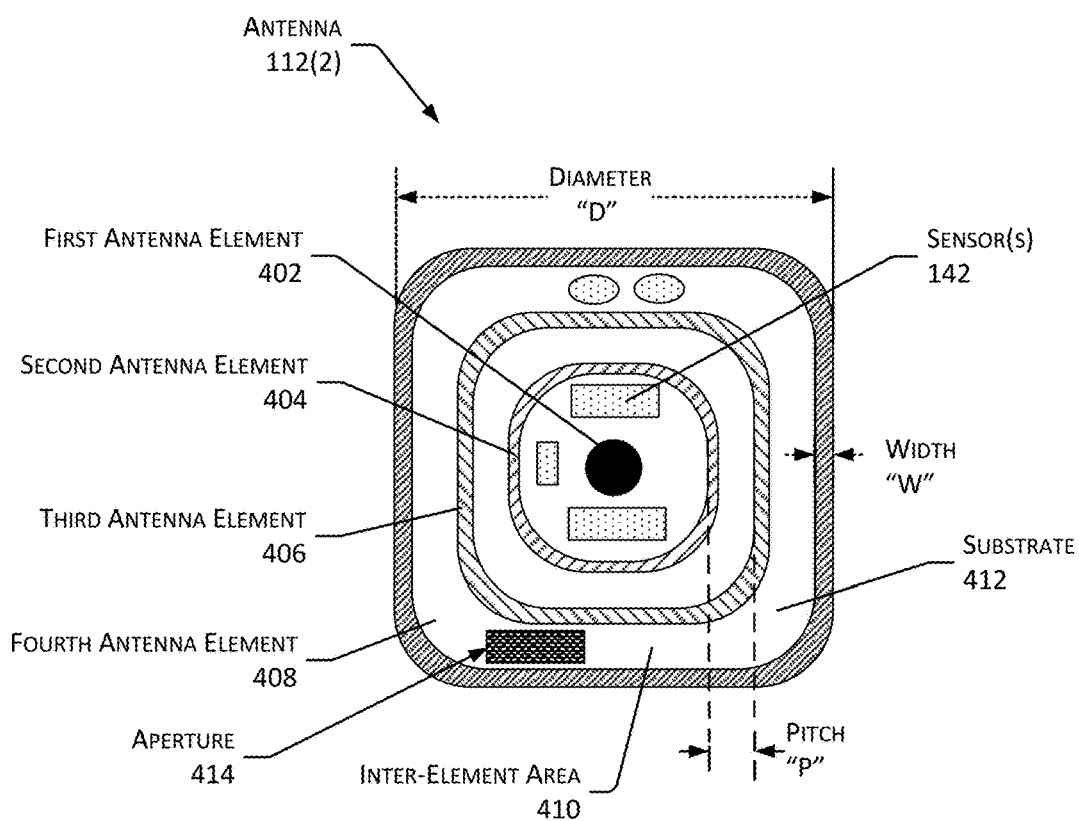

FIG. 4 illustrates plan views of some implementations of antenna elements in the antenna.

A first implementation of an antenna 112(1) is shown that comprises a first antenna element 402, a second antenna element 404, a third antenna element 406, and a fourth antenna element 408. The second antenna element 404 is arranged around the first antenna element 402. The third antenna element 406 is arranged around the second antenna element 404. The fourth antenna element 408 is arranged around the third antenna element 406. In this implementation, the first antenna element 402 is circular. The other antenna elements 404-408 comprise concentric rings that are centered on the first antenna element 402. In other implementations, one or more of the antenna elements may not be centered with respect to one another. Antenna elements in the antenna 112 may be electrically separated to avoid an electrically conductive path between antenna elements.

The antenna 112(1) exhibits a diameter "D" that extends from opposite outside edges of the fourth antenna element 408. Each antenna element has a width "W". In some implementations, the width "W" may vary by antenna element. For example, a width of the second antenna element 404 may be less than a width of the third antenna element 406. Also shown is a pitch "P" between similar features on adjacent antenna elements. For example, the pitch "P" may be measured from an inner edge of adjacent antenna elements.

A second implementation of antenna 112(2) is shown that comprises a first antenna element 402, a second antenna element 404, a third antenna element 406, and a fourth antenna element 408. The second antenna element 404 is arranged around the first antenna element 402. The third antenna element 406 is arranged around the second antenna element 404. The fourth antenna element 408 is arranged around the third antenna element 406. In this implementation, the first antenna element 402 is circular. The other antenna elements 404-408 are rectangular with rounded corners having a radius of curvature. In some implementations the radius of curvature may be equal to or greater than 1 mm. The antenna elements 404-408 are centered on the first antenna element 402.

An inter-element area 410 is shown between two adjacent antenna elements. For example, there is a first inter-element area 410 between the first antenna element 402 and the second antenna element 404, a second inter-element area 410 between the second antenna element 404 and the third antenna element 406, and a third inter-element area 410 between the third antenna element 406 and the fourth antenna element 408.

The antenna 112 may include a substrate 412 that is electrically non-conductive. For example, the substrate 412 may comprise an insulator such as plastic or glass. The antenna elements may be on, affixed to, incorporated within, or otherwise maintained by the substrate 412. The substrate 412 may be rigid or flexible. For example, the substrate 412 may comprise a plastic layer upon which the antenna elements have been deposited. In one implementation the antenna 112 may comprise a flexible printed circuit with the antenna elements comprising traces thereon.

One or more apertures 414 or sensors 142 may be located within the inter-element area 410 of the antenna 112. The aperture 414 may provide a window or opening in the substrate 412 to facilitate operation of the wearable device 104. For example, the aperture 414 may provide a window through which an optical sensor such as a light emitting diode (LED) or a camera 142(7) is able to operate and acquire data about the user 102. In another example, the aperture 414 may be used by another sensor, such as a capacitive sensor, pressure sensor, and so forth. Some devices may be mounted to the substrate 412 or may be located between the antenna 112 and the user 102 during operation. For example, an LED may be affixed to the substrate 412 and when operated may illuminate a portion of the user 102 that is proximate to the inner surface of the wearable device 104. In some implementations sensors may operate through the substrate. For example, if the substrate is flexible a pressure sensor may operate through the substrate. In another example the substrate may be transmissive to a signal being detected, such as a particular frequency of light.

The antenna 112 may comprise two or more antenna elements. While four antenna elements are depicted here, in other implementations the antenna 112 may include more or fewer antenna elements. In some implementations arrays of antennas 112 may be used. The arrays may include antennas 112 with different dimensions. For example, a first antenna 112(4) may have a maximum outermost diameter of 10 mm while a second antenna 112(5) has a maximum outermost diameter of 5 mm.

One or more of the antenna elements may include three or more corners with a radius of curvature equal to or greater than one millimeter. For example, antenna elements 404-408 may each have a rounded triangular shape, a rounded hexagon, and so forth.

The diameter D may be determined based on the sample depth desired during operation. For example, if the first antenna element 402 is used to emit the signal 108, the signal 108 may penetrate the portion of the user 102 that is proximate to the antenna 112 to a depth that is approximately equal to the diameter of the antenna element used to acquire the signal 108. In one implementation the outermost antenna element may have a diameter of 10 mm.

One or more of the antenna elements may comprise closed loops as shown here. For example, the first antenna element 402 may comprise a circular area while the second antenna element 404 comprises an electrically conductive ring. In other implementations, the antenna element 402 may have at least one gap or electrically non-conductive region to form a split ring.

Figure 5:
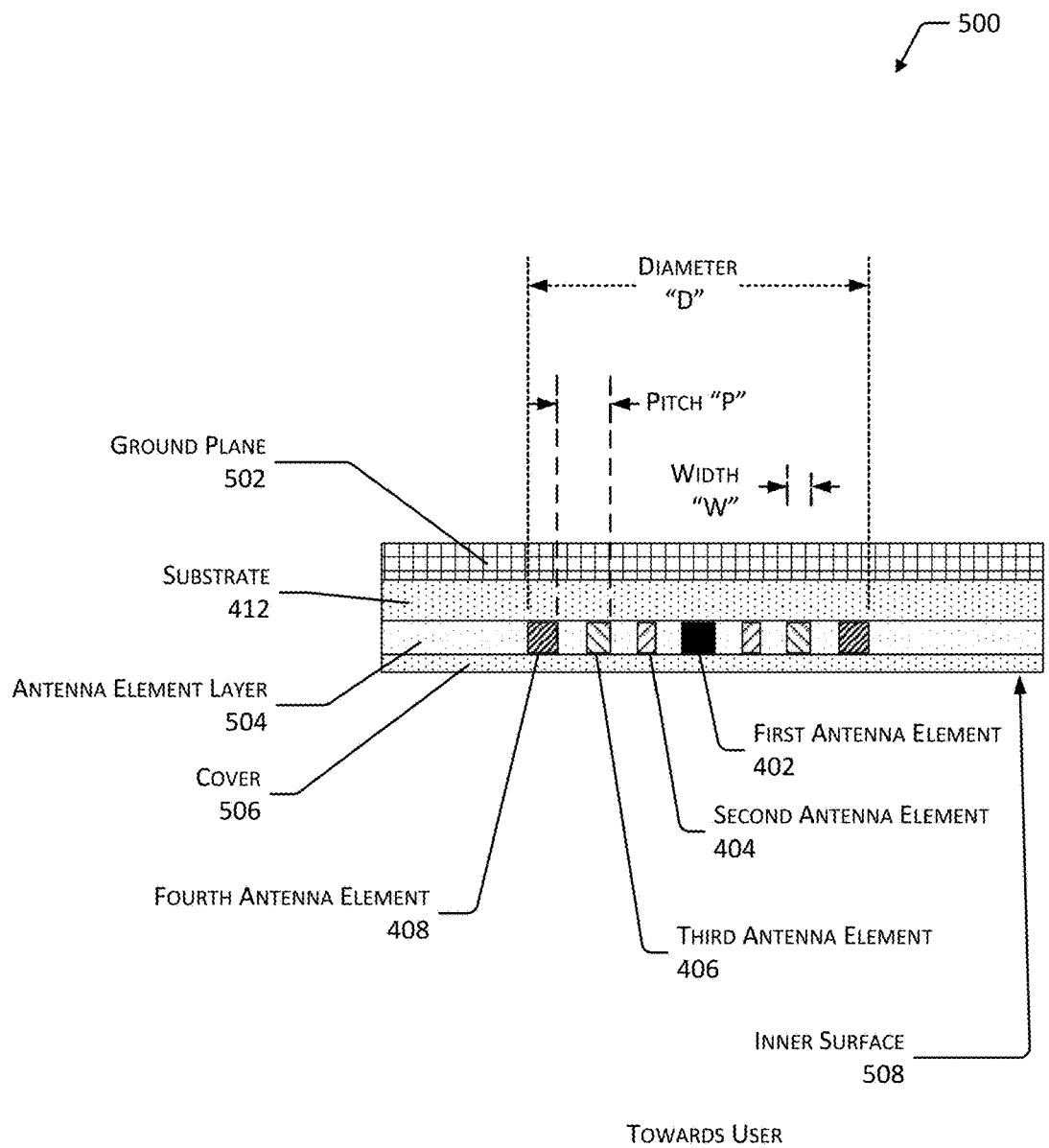
FIG. 5 illustrates a cross section of the antenna, according to one implementation.

FIG. 5 illustrates a cross section 500 of the antenna 112(1), according to one implementation. As described with regard to FIG. 4, the antenna 112(1) comprises the first antenna element 402, the second antenna element 404, the third antenna element 406, and the fourth antenna element 408 that are supported by the substrate 412. In some implementations the system may include a ground plane 502 or shield that is located behind the substrate 412, on a side opposite where the user 102 will be during use. For example, the ground plane 502 may comprise a sheet of electrically conductive material.

The antenna elements may be located in a common plane, which may be designated as an antenna element layer 504. In other implementations one or more of the antenna elements may be positioned at different heights or have different thicknesses with respect to the substrate 412.

A cover 506 may be used that is adjacent to the antenna elements and is between the antenna elements and the user 102. The cover 506 may comprise a non-conductive material. For example, the cover 506 may comprise plastic, glass, or another material that is transparent to the signal(s) 108. In some implementations the cover 506 may be omitted. In this implementation, the antenna elements may come into direct contact with the skin of the user 102. The antenna elements may comprise a biocompatible material such as gold, silver, rhodium, and so forth. In addition to being used to emit and acquire the signal 108, in implementations where the antenna elements are in contact with the user 102, they may be used to acquire other information. For example, galvanic skin conductivity may be measured using two or more antenna elements, cardiac electrical signals may be acquired using one or more of the antenna elements, and so forth.

An inner surface 508 of the antenna 112(1) is proximate to a portion of the user 102 while the wearable device 104 is being worn.

Figure 6:
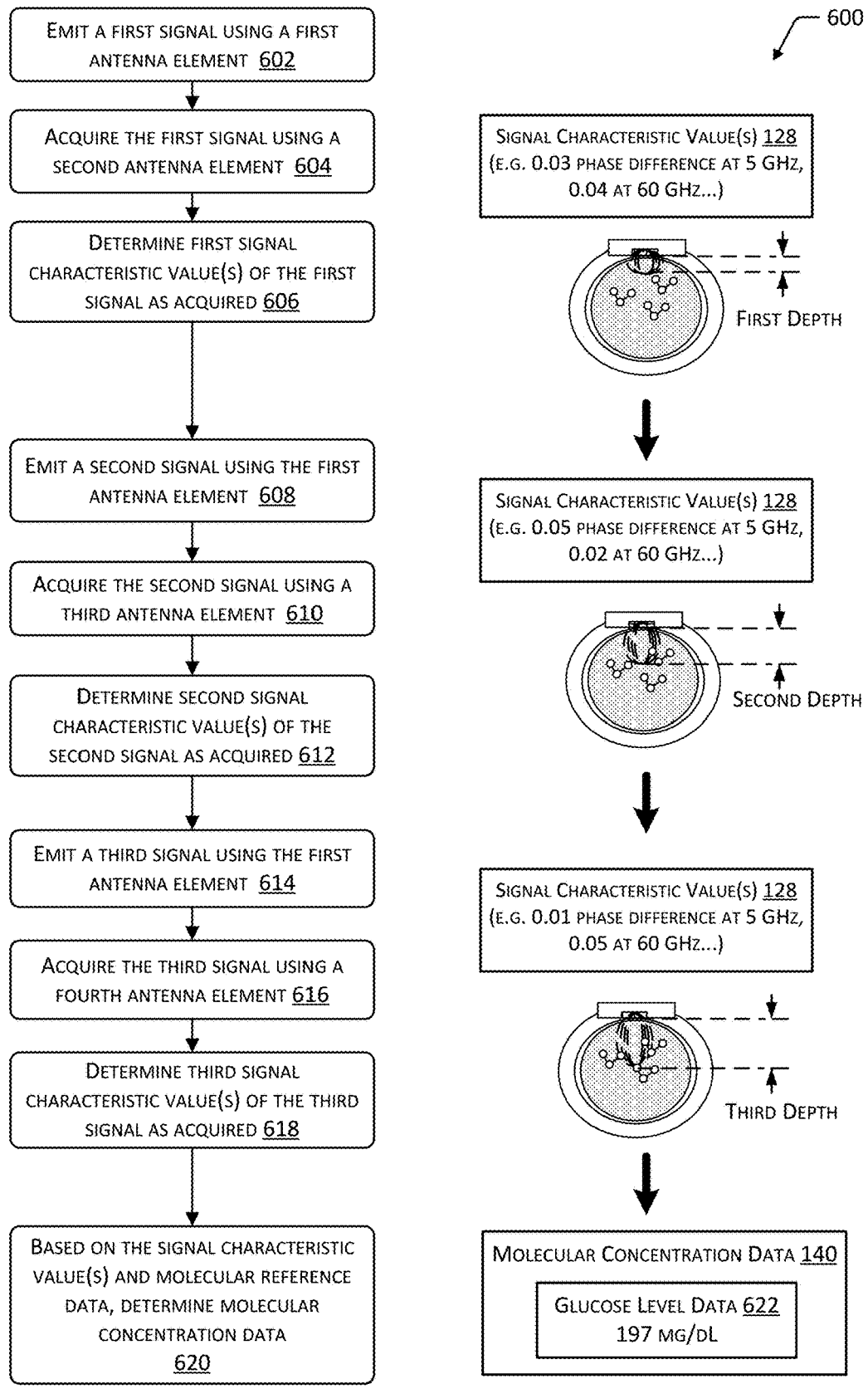
FIG. 6 illustrates a flow diagram of a process of selectively using different antenna elements to acquire data from different depths within the user, according to one implementation.

FIG. 6 illustrates a flow diagram 600 of a process of selectively using different antenna elements to acquire data from different depths within the user 102, according to one implementation. The process may be implemented at least in part by the wearable device 104 using the antenna 112.

At 602 a first signal 108 is emitted using a first antenna element 402. At least a portion of the first signal 108 may penetrate at least a portion of the user 102. As described above, the sample depth may be determined at least in part by the diameter of the antenna element. For example, if the first antenna element 402 is in the center of the antenna 112 and is used to transmit, the approximate sample depth may be the diameter of the second antenna element 404. The operation of switching devices to produce a particular configuration of antennas for emitting and acquiring signals 108 may be determined based at least in part on the sample depth.

For example, the antenna element used to emit the signal 108 may be connected to the transmitter 118 with a switching device in some implementations. The switching device may allow the output of the transmitter 118 to be selectively coupled to one or more elements in the antenna 112. In another example, a switching device may be used to selectively connect one or more of the elements of the antenna 112 to the receiver 120.

At 604 the first signal 108 is acquired using a second antenna element 404.

At 606 a first signal characteristic value(s) 128 is determined. For example, a phase difference may be determined for the first signal 108 by determining a difference in phase between the first signal 108 as generated by the transmitter 118 and the first signal 108 as received by the receiver 120. The first signal characteristic value(s) 128 comprises information about the molecules 106 from the antenna 112 to approximately a first sample depth.

At 608 a second signal 108 is emitted using the first antenna element 402. At least a portion of the second signal 108 may penetrate at least a portion of the user 102.

At 610 the second signal 108 is acquired using a third antenna element 406. As described above, the sample depth may be determined at least in part by the diameter of the antenna element used to acquire the signal 108. For example, if the first antenna element 402 is in the center of the antenna 112 and is used to transmit, the approximate sample depth may be the diameter of the third antenna element 406.

At 612 a second signal characteristic value(s) 128 is determined. For example, a phase difference may be determined for the second signal 108 by determining a difference in phase between the second signal 108 as generated by the transmitter 118 and the second signal 108 as received by the receiver 120. The second signal characteristic value(s) 128 comprises information about the molecules 106 from the antenna 112 to approximately a second sample depth. Continuing the example, if the third antenna element 406 is greater in diameter than the second antenna element 404, the second sample depth is greater than the first sample depth.

At 614 a third signal 108 is emitted using the first antenna element 402. At least a portion of the third signal 108 may penetrate at least a portion of the user 102.

At 616 the third signal 108 is acquired using a fourth antenna element 408. As described above, the sample depth may be determined at least in part by the diameter of the antenna element used to acquire the signal 108. For example, if the first antenna element 402 is in the center of the antenna 112 and is used to transmit, the approximate sample depth may be the diameter of the fourth antenna element 408.

At 618 a third signal characteristic value(s) 128 is determined. For example, a phase difference may be determined for the third signal 108 by determining a difference in phase between the third signal 108 as generated by the transmitter 118 and the third signal 108 as received by the receiver 120. The third signal characteristic value(s) 128 comprises information about the molecules 106 from the antenna 112 to approximately a third sample depth. Continuing the example, if the fourth antenna element 408 is greater in diameter than the third antenna element 406, the third sample depth is greater than the second sample depth.

At 620, based on the signal characteristic values 128 the molecular concentration data 140 is determined for the user 102. For example, the signal characteristic values 128 may be used as inputs to the molecular reference data 138 which provides as output the molecular concentration data 140. Continuing the example, the molecular concentration data 140 may include glucose level data 622. In another example the signal characteristic value(s) 128 may be provided as input to a machine learning system which then provides as output the molecular concentration data 140.

Figure 7:
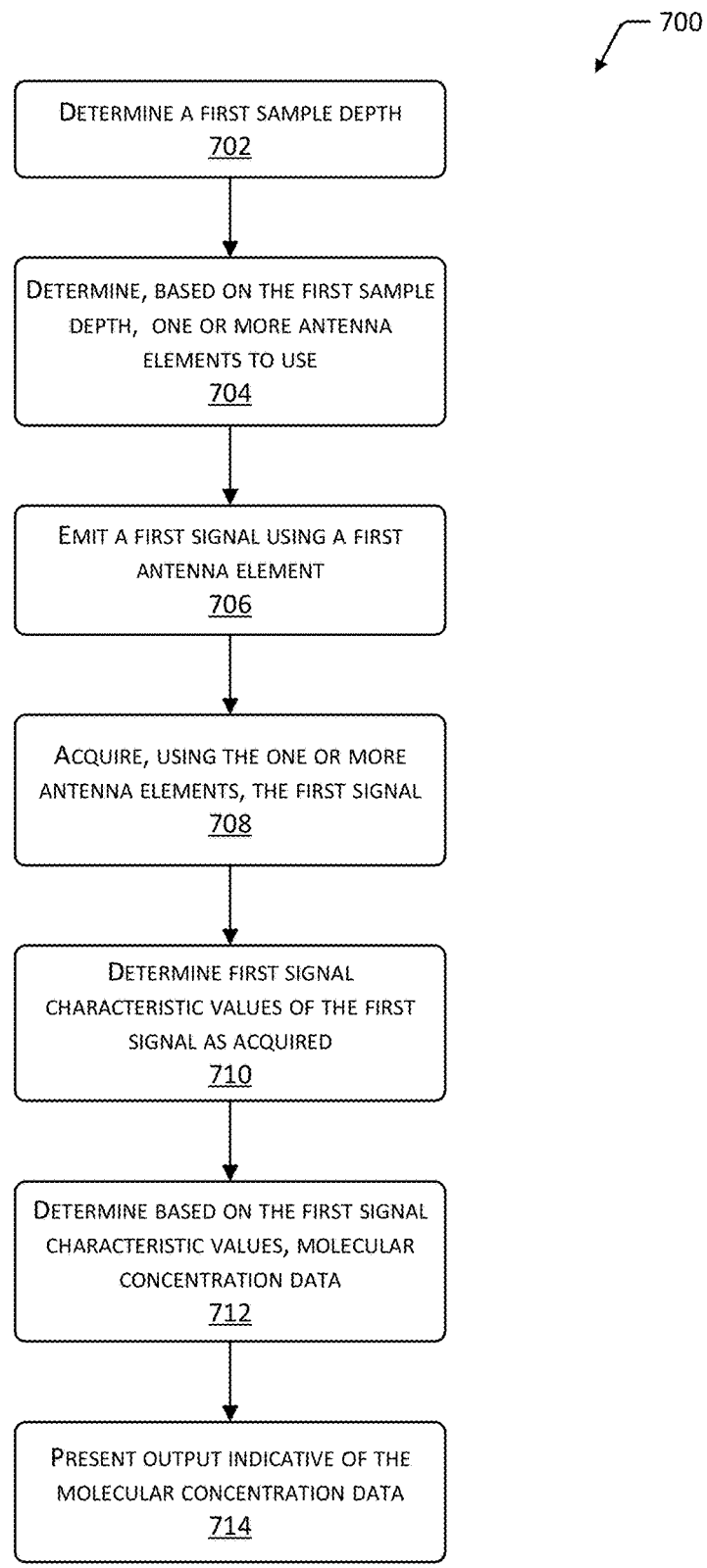
FIG. 7 illustrates a flow diagram of a process of using radio frequency signals emitted and acquired by the antenna to determine molecular concentration data, according to one implementation.

FIG. 7 illustrates a flow diagram 700 of a process of using radio frequency signals 108 emitted and acquired by the antenna 112 to determine molecular concentration data 140, according to one implementation. The process may be implemented at least in part by the wearable device 104.

At 702 a first sample depth is determined. For example, the sample depth may be determined based on a type of molecule 106 that is being measured, data from one or more of the other sensors 142, and so forth. For example, the sample depth may be determined based on sensor output from the temperature sensor 142(6). A first sample depth may be determined if the user's 102 temperature is within a first range of temperatures while a second sample depth may be determined if the user's 102 temperature is within a second range of temperatures. In another example, the sample depth may be determined based on the amplitude and duration of motion as indicated by the accelerometer 142 (10). For example, if amplitude and duration of motion is less than a first threshold value, a first sample depth may be determined. If the amplitude and duration of motion is greater than the first threshold value, a second sample depth may be determined. In still another example, the sample depth may be provided based on information about the user 102. For example, the sample depth may be determined based on the diameter of the user's 102 wrist.

At 704, based on the first sample depth, a determination is made as to which of the one or more of the antenna elements to use. In one implementation, an antenna configuration may be determined based on the first sample depth. The antenna configuration may be indicative of a first set of one or more antenna elements to connect to the transmitter 118 and a second set of one or more antenna elements to connect to the receiver 120. For example, the antenna configuration may indicate that the first antenna element 402 is to be connected to the output of the transmitter 118 while the fourth antenna element 408 is to be connected to the input of the receiver 120. The circuitry in the wearable device 104 may be operated to establish the connections as specified by the antenna configuration.

At 706 a first signal 108 is emitted using the first antenna element 402. For example, the transmitter 118 may generate the signal 108 which is provided to the first antenna element 402 which emits or radiates the signal 108 towards the user 102.

At 708, the first signal is acquired using the one or more antenna elements. In some implementations, the first signal may be acquired using antenna elements not connected to the transmitter. For example, the first signal 108 may be acquired by the fourth antenna element 408. In other implementations one or more directional couplers, duplexers, or other devices may be used to acquire the first signal using the first antenna element 402 of the antenna 112.

At 710 first signal characteristic values 128 of the first signal as acquired are determined. For example, the signal characteristic values 128 may include frequency data 130, phase data 132, amplitude data 134, and so forth.

At 712, based on the first signal characteristic values 128, molecular concentration data 140 is determined. For example, the first signal characteristics values 128 may be used as input to the molecular reference data 138 to determine a corresponding concentration of a particular type of molecule 106.

At 714 output indicative of the molecular concentration data 140 is presented. In one implementation, the user interface module 144 may generate output data 146 that is used by the one or more output devices 148 to present output to the user 102. For example, a graphical indication may be provided using a display device 148(3) of the other device 150.

While the system and techniques described herein are used with respect to measure humans, it is understood that these techniques may be used to monitor other types of organisms, such as animals. In some implementations, the systems and techniques may be used to characterize other objects. For example, the system may be used to determine a sugar concentration in a fruit, water concentration in a mixture, and so forth.

The processes discussed herein may be implemented in hardware, software, or a combination thereof. In the context of software, the described operations represent computer-executable instructions stored on one or more non-transitory computer-readable storage media that, when executed by one or more processors, perform the recited operations.

Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described herein. The computer-readable storage medium may be one or more of an electronic storage medium, a magnetic storage medium, an optical storage medium, a quantum storage medium, and so forth. For example, the computer-readable storage media may include, but is not limited to, hard drives, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Thus, although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as illustrative forms of implementing the claims.

What is claimed is:

1. A wearable device comprising:
a first antenna element affixed to a substrate;
a second antenna element affixed to the substrate, wherein the second antenna element is arranged concentrically around the first antenna element;
a third antenna element affixed to the substrate, wherein the third antenna element is arranged concentrically around the second antenna element;
a transmitter connected to the first antenna element;
a switching device comprising:
an output, and
a first input connected to the second antenna element and a second input connected to the third antenna element;
a receiver connected to the output of the switching device;
a first memory storing computer-executable instructions; and
a first hardware processor, wherein the first hardware processor executes the computer-executable instructions to:
operate the switching device to connect the receiver to the second antenna element at a first time;
operate the transmitter to generate a first signal at the first time;
operate the receiver at the first time to receive the first signal;
determine a first phase difference of the first signal as received by the receiver relative to the first signal generated by the transmitter;
operate the switching device to connect the receiver to the third antenna element at a second time;
operate the transmitter to generate a second signal at the second time;
operate the receiver at the second time to receive the second signal;
determine a second phase difference of the second signal as received by the receiver relative to the second signal generated by the transmitter; and
determine, using the first phase difference and the second phase difference, a concentration value of a type of molecule.

2. The wearable device of claim 1, further comprising:
a non-conductive cover that is adjacent to one or more of the first antenna element, the second antenna element, or the third antenna element.

3. A wearable device comprising:
a first antenna element on a substrate;
a second antenna element on the substrate, the second antenna element arranged around the first antenna element;
a third antenna element on the substrate, the third antenna element arranged around the second antenna element;
a transmitter having an output;
a receiver having an input;
first circuitry to couple the output of the transmitter to a first one of the first antenna element, the second antenna element, or the third antenna element;
second circuitry to couple the input of the receiver to:
a second one of the first antenna element, the second antenna element, or the third antenna element; or
a third one of the first antenna element, the second antenna element, or the third antenna element;
a first memory storing computer-executable instructions; and
a first hardware processor, wherein the first hardware processor executes the computer-executable instructions to:
operate the first circuitry, at a first time, to couple the output of the transmitter to the first one of the first antenna element, the second antenna element, or the third antenna element;
operate the second circuitry, at the first time, to couple the input of the receiver to the second one of the first antenna element, the second antenna element, or the third antenna element;

operate the transmitter to generate a first signal;
operate the receiver to receive the first signal;
determine one or more first signal characteristic values of the first signal as received by the receiver;
operate the second circuitry, at a second time, to couple the input of the receiver to the third one of the first antenna element, the second antenna element, or the third antenna element;
operate the transmitter to generate a second signal;
operate the receiver to receive the second signal;
determine one or more second signal characteristic values of the second signal as received by the receiver; and
determine, using the one or more first signal characteristic values and the one or more second signal characteristics values, a concentration value of a type of molecule.

4. The wearable device of claim 3, further comprising:
a pressure sensor; and
wherein the first hardware processor further executes the computer-executable instructions to:
receive data from the pressure sensor;
determine, based on the data, that at least a portion of the wearable device is in contact with an object; and
wherein the computer-executable instructions to operate one or more of the transmitter or the receiver are based at least in part on the at least a portion of the wearable device being in contact with the object.

5. The wearable device of claim 3, wherein the one or more first signal characteristic values are indicative of one or more of:
a phase difference,
a received signal amplitude, or
a received signal polarization.

6. The wearable device of claim 3, wherein the first hardware processor further executes the computer-executable instructions to:
operate the first circuitry, at the first time, to couple the output of the transmitter to the first antenna element; and
operate the second circuitry, at the first time, to couple the input of the receiver to one of the second antenna element or the third antenna element.

7. The wearable device of claim 3, wherein the first hardware processor further executes the computer-executable instructions to:
operate the first circuitry, at the first time, to couple the output of the transmitter to the third antenna element; and
operate the second circuitry, at the first time, to couple the input of the receiver to one of the first antenna element or the second antenna element.

8. The wearable device of claim 3, wherein the first hardware processor further executes the computer-executable instructions to:
determine a first sample depth;
determine, based on the first sample depth, an antenna configuration indicative of the first one of the first antenna element, the second antenna element, or the third antenna element to connect to the transmitter and the second and third ones of the first antenna element, the second antenna element, or the third antenna element to connect to the receiver; and
operate the first circuitry and the second circuitry based on the antenna configuration.

9. The wearable device of claim 3, wherein the first antenna element is circular, the second antenna element is arranged concentrically around and centered on the first antenna element, and the third antenna element is arranged concentrically around and centered on the second antenna element.

10. The wearable device of claim 3, wherein:
the first antenna element has at least three corners,
the second antenna element has at least three corners, and
the third antenna element has at least three corners.

11. The wearable device of claim 3, wherein the first antenna element, the second antenna element, and the third antenna element each comprise a closed loop.

12. The wearable device of claim 3, further comprising:
an aperture in the substrate between one or more of:
the first antenna element and the second antenna element, or
the second antenna element and the third antenna element; and
an optical sensor proximate to the aperture.

13. The wearable device of claim 3, further comprising:
a cover, wherein the first antenna element, the second antenna element, and the third antenna element are between the cover and the substrate.

14. A wearable device comprising:
a first antenna element;
a second antenna element, the second antenna element arranged around the first antenna element;
a third antenna element, the third antenna element arranged around the second antenna element;
a transmitter having an output;
a receiver having an input;
first circuitry to couple the output of the transmitter to a first one of the first antenna element, the second antenna element, or the third antenna element;
second circuitry to couple the input of the receiver to:
a second one of the first antenna element, the second antenna element, or the third antenna element, or
a third one of the first antenna element, the second antenna element, or the third antenna element;
at least one memory storing computer-executable instructions; and
at least one hardware processor, wherein the at least one hardware processor executes the computer-executable instructions to:
operate the first circuitry, at a first time, to couple the output of the transmitter to the first one of the first antenna element, the second antenna element, or the third antenna element;
operate the second circuitry, at the first time, to couple the input of the receiver to the second one of the first antenna element, the second antenna element, or the third antenna element;
operate the transmitter to generate a first signal;
operate the receiver to receive the first signal;
determine one or more first signal characteristic values of the first signal as received by the receiver;
operate the second circuitry, at a second time, to couple the input of the receiver to the third one of the first antenna element, the second antenna element, or the third antenna element;
operate the transmitter to generate a second signal;
operate the receiver to receive the second signal; and
determine one or more second signal characteristic values of the second signal as received by the receiver.

15. The wearable device of claim 14, wherein the first antenna element, the second antenna element, and the third antenna element are arranged in a common plane.

16. The wearable device of claim 14, wherein the first, second, and third ones of the first antenna element, the second antenna element, or the third antenna element are different antenna elements.

17. The wearable device of claim 14, wherein the at least one hardware processor further executes the computer-executable instructions to:
operate the first circuitry, at the first time, to couple the output of the transmitter to the first antenna element; and
operate the second circuitry, at the first time, to couple the input of the receiver to one of the second antenna element or the third antenna element.

18. The wearable device of claim 14, wherein the at least one hardware processor further executes the computer-executable instructions to:
operate the first circuitry, at the first time, to couple the output of the transmitter to the third antenna element; and
operate the second circuitry, at the first time, to couple the input of the receiver to one of the first antenna element or the second antenna element.

19. The wearable device of claim 14, wherein the at least one hardware processor further executes the computer-executable instructions to:
determine a first sample depth to sample;
determine, based on the first sample depth, an antenna configuration indicative of the first one of the first antenna element, the second antenna element, or the third antenna element to connect to the transmitter and the second and third ones of the first antenna element, the second antenna element, or the third antenna element to connect to the receiver; and
operate the first circuitry and the second circuitry based on the antenna configuration.

20. The wearable device of claim 14, further comprising:
a substrate, wherein the first antenna element, the second antenna element, and the third antenna element are on the substrate;
an aperture in the substrate between one or more of:
the first antenna element and the second antenna element, or
the second antenna element and the third antenna element; and
a sensor proximate to the aperture.

* * * * *